United States Patent [19]

Grollimund

[11] Patent Number: 4,665,915

[45] Date of Patent: May 19, 1987

[54] FLESH CUTTER OF STRIP FOR GRAFTING

[76] Inventor: Everett C. Grollimund, 3306 Nuttree Woods Pl., Midlothian, Va. 23113

[21] Appl. No.: 816,215

[22] Filed: Jan. 6, 1986

Related U.S. Application Data

[63] Continuation-in-part of Ser. No. 549,304, Nov. 7, 1983, abandoned.

[51] Int. Cl.⁴ .......................................... A61B 17/322
[52] U.S. Cl. .................................................. 128/305.5
[58] Field of Search ...................... 128/305.5, 305, 304, 128/355, 751, 757; 30/282, 284, 285, 286, 294, 121, 280, 278, 337, 339; 17/62, 21, 50

[56] References Cited

U.S. PATENT DOCUMENTS

| | | | |
|---|---|---|---|
| 1,062,945 | 5/1913 | Anderson | 30/280 |
| 2,222,036 | 11/1940 | Koppin et al. | 30/280 |
| 2,309,444 | 1/1943 | De Vault | 30/280 |
| 3,099,307 | 7/1963 | Morgan | 30/294 X |
| 3,934,591 | 1/1976 | Gleason | 128/305.5 |
| 4,038,986 | 8/1977 | Makler | 128/305.5 |

FOREIGN PATENT DOCUMENTS

| | | | |
|---|---|---|---|
| 840886 | 6/1952 | Fed. Rep. of Germany | 128/305 |
| 972146 | 1/1951 | France | 128/304 |

Primary Examiner—Michael H. Thaler
Attorney, Agent, or Firm—John F. C. Glenn

[57] ABSTRACT

Gingival graft cutter has continuous contoured blade carried on skids and directed by pivotally connected handle, to produce graft tissue in strips of uniform cross-section.

15 Claims, 19 Drawing Figures

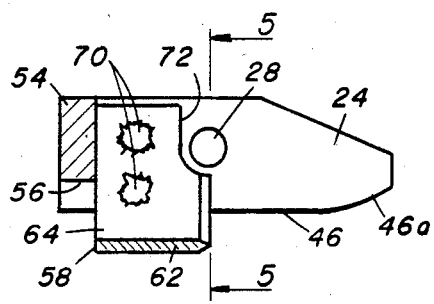
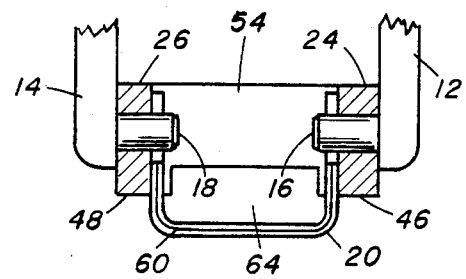
FIG. 4     FIG. 5
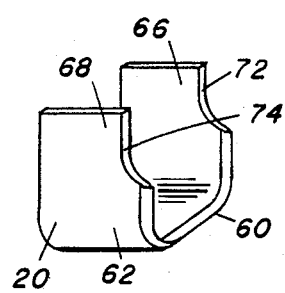
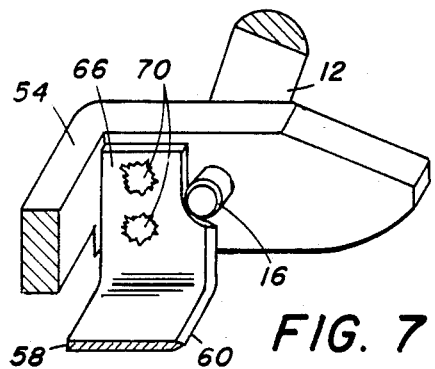
FIG. 6     FIG. 7
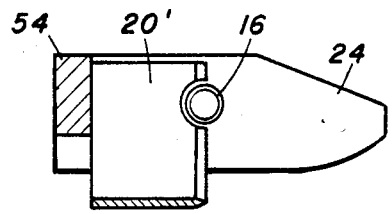
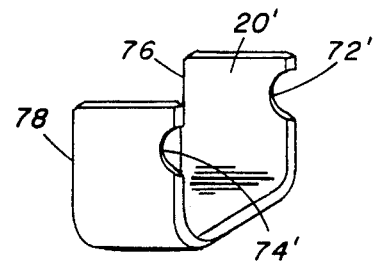
FIG. 8     FIG. 9
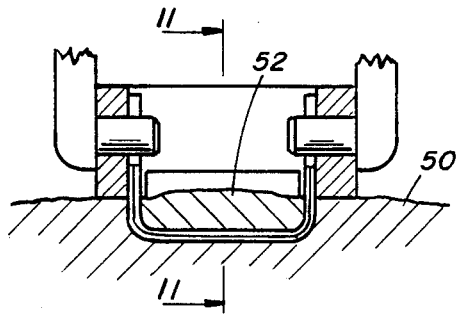
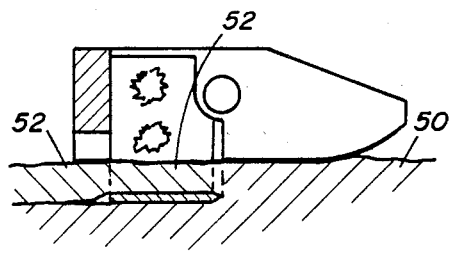
FIG. 10    FIG. 11

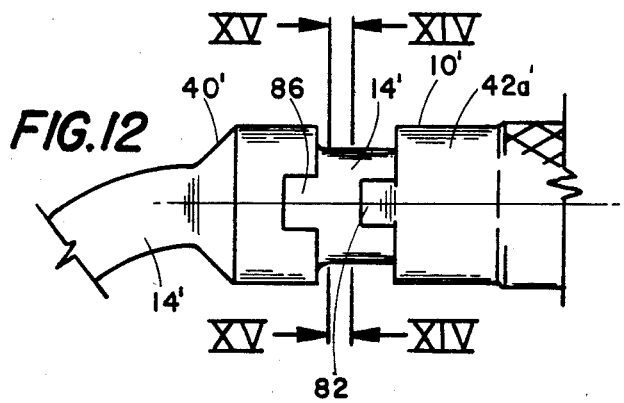
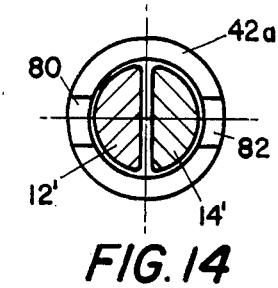
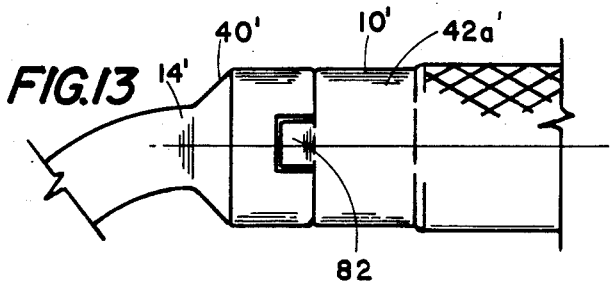
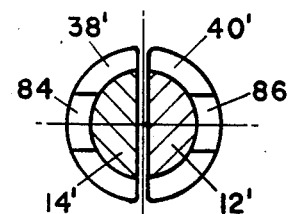
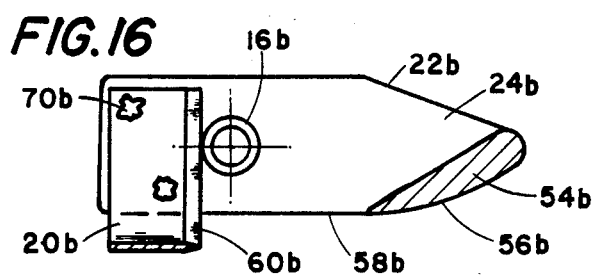
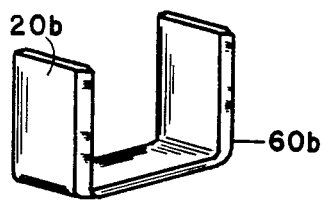
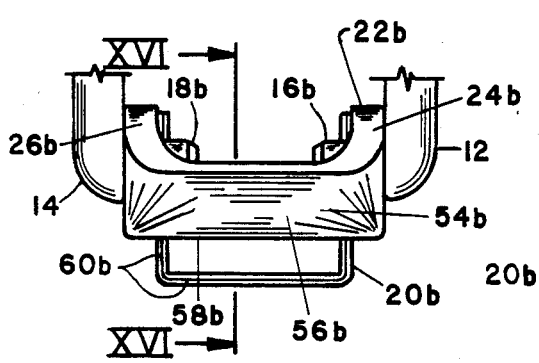
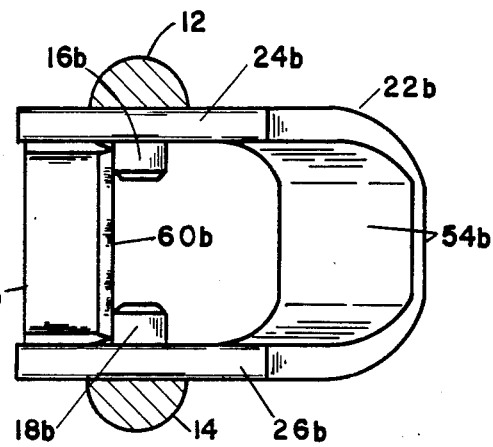

FLESH CUTTER OF STRIP FOR GRAFTING

This is a continuation-in-part of application Ser. No. 06/549,304, filed Nov. 7, 1983, now abandoned.

BACKGROUND OF THE INVENTION

In peridontal surgery, the technique of using the free autogenous gingival graft has been the most used and preferred method of supplementing the attached gingival tissue. The procedure involves removing a precise piece of donor tissue from the hard palate and grafting it to increase the dimension of the attached gingiva in a deficient area. Because of the difficult area to work in the mouth and the precise dimension of the donor tissue, improved cutting instruments are needed to improve and simplify the technique.

Various attempts to improve cutting instruments for gingival and other human tissue for grafting purposes are exemplified in U.S. Pat. Nos. 2,236,067 (Foth), 2,442,435 (Reese), 3,013,553 (Averbach), 3,327,711 (Vallis), 3,412,732 (Simon), 3,583,403 (Pohl et al.), 3,670,734 (Hardy), 3,688,407 (Paquette), 3,797,505 (Gilhaus) 3,934,591 (Gleason), 4,038,986 (Mahler), 4,098,278 (Schwartz), 4,221,222 (Detsch) and 4,240,432 (Mormann et al.).

SUMMARY OF THE INVENTION

In accordance with the present invention, a cutting instrument is provided which can be operated to cut a strip conveniently and accurately from a body of material, such as to cut donor tissue from a donor site. The instrument has a handle which may be grasped by one hand, and a cutting blade held by a carrier having skid surfaces which are slidable over such body to position and guide the blade relative to the body during the cutting action. The blade carrier is pivotally connected to the handle so that it can tilt relative to the handle and thereby permit the carrier to tilt as it slides over an undulating surface without corresponding angular motion of the handle. Thus, the operator merely supplies the desired pressure and moving force to the support and attached blade, without having to control the angle of the blade.

The blade cutting edge projects beneath the skid surfaces of the carrier and forms an open-ended passage of undiminished cross-section between the projection portion of the blade and the level of the skid surfaces. The carrier is preferably relieved to extend this passage partially above the level of the skid surfaces, to accommodate the tendency of the tissue between the skids to bulge up between them when the skids are pressed down. The blade body behind the cutting edge is in the form of a strip which trails behind the edge in line with the edge cutting movement. This, together with the thinness of the blade, which is preferably conventional flexible razor blade stock, enable the blade to cut a strip which is of substantially uniform cross-section, and which passes substantially straight through said open ended passage. This avoids curling of the strip, and thus makes such a strip cut from human tissue more convenient to handle for grafting purposes.

Other objects, advantages and details of the invention will become apparent as the following description of the invention proceeds.

BRIEF DESCRIPTION OF THE DRAWINGS

The accompanying drawings show present preferred embodiments of the invention in the following figures.

FIG. 4 shows a section of the blade holder taken on the line IV—IV in FIG. 1, omitting the adjacent gripping arm and its pivot pin;

FIG. 5 shows a section of the blade holder taken on the line V—V in FIG. 2, including the adjacent gripping arm portions and their pivot pins;

FIG. 6 shows an isometric view of the blade shown in FIGS. 1-5;

FIG. 7 shows an isometric view of a portion of the blade, holder and releasable gripping arm of the holder adjacent a pivoted connection of the arm to the holder and to the welded connection to the blade;

FIG. 8 is a view corresponding to FIG. 4, but showing a modified form of blade mechanically secured to the holder;

FIG. 9 shows a view corresponding to FIG. 6, but showing the modified form of blade shown in FIG. 8;

FIG. 10 shows a view corresponding to FIG. 5, but including a cross-section of a body of material and a strip being cut from it by the instrument; and FIG. 11 shows a section taken on the line XI—XI in FIG. 10.

FIG. 12 shows a side view, partially broken away, of a modified form of handle, in partially retracted positions;

FIG. 13 shows a view corresponding to FIG. 12, but with the modified handle in operating position;

FIG. 14 shows a section on the line XIV—XIV in FIG. 12;

FIG. 15 shows a section on the line XV—XV in FIG. 12;

FIG. 16 shows a side view of a modified form of blade and blade holder;

FIG. 17 shows an end view seen from the right of FIG. 16;

FIG. 19 shows an isometric view of the blade shown in FIGS. 16 and 17; and

FIG. 18 shows a top plan view of the blade and holder shown in FIGS. 16 and 17.

DETAILED DESCRIPTION OF PRESENT PREFERRED EMBODIMENTS

Figure 1:
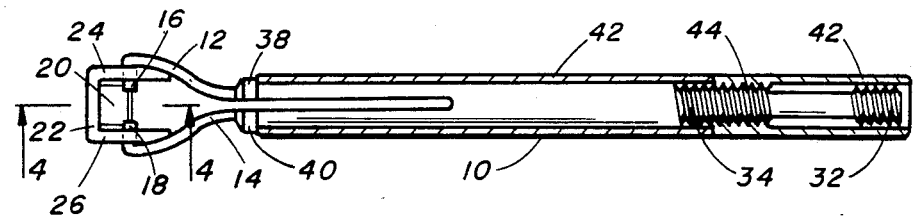
FIG. 1 shows a top plan view, partially sectioned, of a cutting instrument in accordance with the invention, having a cutting blade, a blade holder and a handle having releasable gripping arms.
Figure 2:
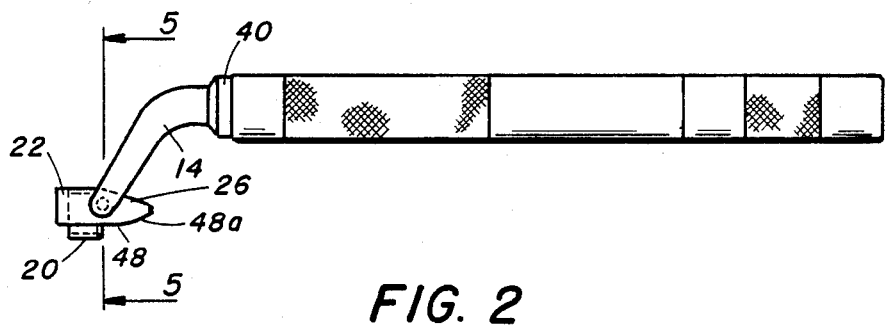
FIG. 2 shows a side view of the instrument shown in FIG. 1.

Referring now more particularly to the drawings, and initally to FIGS. 1 and 2, there is provided a cutting instrument having a tubular operating handle 10, a pair of arms 12 and 14 on which are respectively mounted pins 16 and 18, a blade 20 and a blade carrier 22. The carrier 22 has a pair of sidewalls 24 and 26 having a pair of openings 28 therethrough aligned with a common axis. When the arms 12 and 14 are moved to their holding position shown in FIGS. 1 and 2, the pins 16 and 18 are aligned with each other and can readily be projected through the openings 28 in carrier walls 24 and 26 to pivotally connect the arms 12 and 14 to the carrier 22. When this connection is made the pivotal axis of carrier 22 relative to handle 10 is through the central axis of the pins 16 and 18 and openings 28. The geometry of this construction is such that the pivotal axis of the pins 16 and 18 in openings 28 is parallel to any line which intersects the center line through handle 10 at right angles to the center line, and which also lies in a plane parallel to the said pivotal axis. However, it should be observed that this pivotal connection between the carrier and handle does not have to be so limited if a different degree of control by the user is desired.

Figure 3:
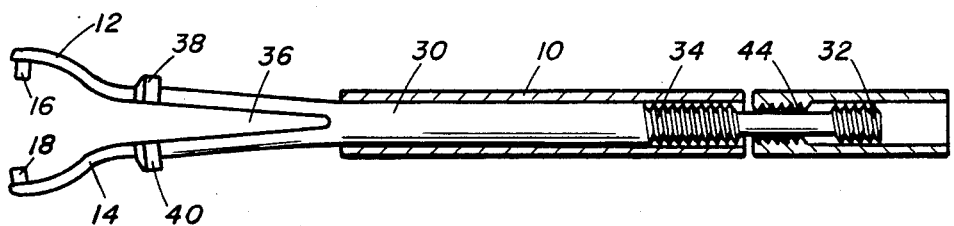
FIG. 3 shows a top plan view of the handle of FIG. 1, but showing only the handle and the gripping arms in open position.

The folding arms 12 and 14 of handle 10 project integrally from one end of a rod 30 extending through the interior of the handle. The rod 30 has threads 32 around its opposite end, and another set of threads 34 spaced from the threads 32. The rod 30 has a slit 36 where the inner-ends of the arms 12 and 14 come together. When the arms are unconfined they are resiliently biased to spring apart, as illustrated in FIG. 3. In that position, which is the open position of the arms, the space between the inner ends of pins 16 and 18 is greater than the width of carrier 22 across the outer ends of openings 28.

Arm 12 has a half ring 38 integrally secured around half of its periphery where the arm 12 is to be held against the outer arm 14 when the arm ends and the pins 16 and 18 are to be moved toward each other from the open position shown in FIG. 3 to the closed position shown in FIGS. 1 and 2. The outer arm 14 has a corresponding half ring 40 secured to it in a corresponding position. These half rings have shoulders facing away from arms 12 and 14 and abutting one end of an outer tube 42a of handle 10 when the arms 12 and 14 are in closed position as shown in FIGS. 1 and 2. The other end of tube 42a abuts the adjacent end of a tube 42b which has a set of internal threads 44 alternately engageable with spaced threads 32 and 34 of rod 30. Tube 42a has no internal threads and slides freely over rod threads 32 and 34. It is pressed against half rings 38 and 40 at the end of movement of tube 42a toward arms 12 and 14 (FIG. 1) caused by rotating tube 42b relative to rod 30 while their respective threads 44 and 34 are interengaged. The pressure of tube 42a against half rings 38 and 40, and the endwise pressure of tubes provides friction to hold the handle and arms together as a unit while the cutting instrument is in use.

Reverse turning of tube 42b until threads 44 and 34 are disengaged releases tube 42a for sliding movement away from arms 12 and 14 until they spring apart to open position (FIG. 3). Threads 32 prevent tube 42b from coming off of rod 30 until disassembly is desired, at which time tube 42b is slid endwise to cause its threads 44 to engae threads 32 and then is rotated relative to rod 30 to cause threads 44 to engage and move around threads 32 until they are no longer engaged. Tube 42a may then be slid endwise to remove it also from rod 30.

The outside of tube 42 is preferably knurled, to facilitate grasping it by hand. As indicated by differences of cross-hatching shown in FIGS. 1 and 3, the tube 42 may be formed of two tubular components integrally secured together end to end. One of these components (on the right in FIGS. 1 and 2) has the internal threads 44 formed in it, and the rest of it is machined out to avoid contact with the external threads 32 and 34 of rod 30. The other of these components (on the left of FIGS. 1 and 3) is unthreaded and likewise has an internal diameter large enough to avoid contact with the threads 32 and 34 of rod 30.

The rear set of threads 32 of rod 30 are spaced far enough from the threads 34 of rod 30 to avoid engagement with threads 44 of tube 42 during relative lengthwise movement of tube 42 and rod 30 for ordinary purposes of opening and closing arms 12 and 14. However, the rear threads of rod 30 will engage threads 44 of tube 42 and halt relative lengthwise movement going substantially further than necessary for opening arms 12 and 14. If withdrawal of tube 42 from rod 30 is desired, after threads 32 and 44 are engaged they may be rotated relative to each other until threads 44 pass beyond threads 32 as tube 42 moves away from arms 12 and 14. Tube 42 can then be withdrawn entirely from rod 30, to complete their disassembly. Reassembly is readily accomplished by reversing these steps, with threads 44 of tube 42 first being counter-rotated past threads 32 and eventually along threads 34 of rod 30 when arms 12 and 14 are to be closed to insert pins 16 and 18 into openings 28 through the sides 24 and 26 of blade carrier 22.

The openings 28 are preferably positioned about midway between the forward and rear ends of sides 24 and 26 considered in the direction of cutting movement of blade carrier 22. The sides 24 and 26 have elongated bottom surfaces 46 and 48 for sliding against the surface of a body 50 from which blade 20 is to cut a strip 52 (FIGS. 10 and 11). These elongaged surfaces are flat and spaced apart, and extend parallel to each other over all of the length except near the leading ends of sides 24 and 26 (to the right as shown in FIGS. 2, 4, 7, 8, and 11), where the surfaces have upwardly sloped extensions 46a and 48a like the leading ends of the running surfaces of a sled. The walls of sides 24 and 26 are similarly spaced apart and parallel, and their rear ends are integrally connected to opposite ends of a cross member 54 extending between them. The cross member 54 is preferably relieved to raise its bottom surface 56 above the level of skid surfaces 46 and 48, in order to avoid scraping against the top of a strip 52 being cut by blade 20 and thus tending to make the strip curl upwardly as it is successively formed and left behind the moving carrier 22.

The blade 20 has a cutting edge 60 and following intermediate portion 62 extending in a preferably shallow loop below the level of skid surfaces 46 and 48. The upper horizontal and inner side surfaces of intermediate blade portion 62 enclose an open-ended and clear passage 64 from the edge 60 to the trailing end 58 of intermediate blade portion. This clear passage is enlarged by the above-mentioned relief of cross member 54 to raise its lower surface 56.

Edge 60 and intermediate blade portion 62 are bent upwardly adjacent the carrier sides 24 and 26, and end portions 66 and 68 of blade 20 extend upwardly from the level of the skid surfaces 46 and 48 to lie against the inner surfaces of carrier sides 24 and 26. There they are preferably secured by metallurgical bonding, such as spot welds 70 (FIGS. 4 and 7), after the blade 20 has been aligned as desired with blade carrier 22. As shown in FIGS. 4 and 7, the blade is preferably placed with its rear vertical edges against their respective corners formed between carrier sides 24 and 26 where they join cross member 54, and the upper ends of its forward vertical margins are relieved at 72 and 74 to make room for pins 16 and 18.

In the case of the alternative species of blades shown in FIGS. 8 and 9, the blade 20' has semicircular slot 72' and 74' cut in the upper portions of its forward vertical margins.

The edges of the slots 72' and 74' are positioned to fit tightly against pins 16 and 18 while the rear vertical edges 76 and 78 of blade 20' press firmly against the corners formed between cross member 54 and carrier sides 24 and 26. This mechanically locks blade 20' in place on carrier 22, without any welding. This action is aided by using resilient metal for the blade, and forming the bends in it so that there remains a resilient tendency of the upwardly extending portions of the blade to press outwardly against the inside of blade carrier sides 24 and 26. This resilient action holds blade 20' in place on carrier 22 while pins 16 and 18 are inserted through slots 72' and 74' during placement of carrier 22 between the arms 12 and 14.

As shown in the drawings, blade edge 60 is preferably mounted adjacent a plane passing through the pivotal axis of pins 16 and 18 at right angles to skid surfaces 46 and 48. It has also been found, however, that cutting edges 60 can be positioned further back toward the trailing end of carrier 22. However, such rearward displacement should not be more than halfway back toward the trailing ends of skid surfaces 46 and 48.

When such a cutting instrument is used as a gingival graft knife, the present preferred cutting depths are about 1 and 1.5 mm. the width of the cut varies with particular gingival grafting applications, in a range of about 4 to 10 mm, and at present is preferably in the range of about 6 to 9 mm. Such a knife requires relatively little skill on the part of the operator to produce a graft of uniform cross-section in any desired length, quickly and with minimum cutting and loss of blood.

The handle is preferably modified to introduce means to lock against relative rotation between the tube by which the handle is grasped and the arms attached to the blade carrier, so that the person holding the handle can exercise positive control over any swinging movement of the blade carrier about the central axis of the handle. A tongue and groove conection may be used, for example, for this purpose, as shown in FIGS. 12-15. The parts designated 10', 12', 14', 38', 40' and 42a' in these figures correspond to the parts with the same numbers, without the prime mark, in FIGS. 1-3, except that tube 42a' has a pair of tongues 80 and 82 projecting toward half rings 38' and 40', respectively, and these half rings have slots 84 and 86 in them for receiving the respective tongues when tube 42a' is moved from its retracted position (FIG. 12) to its operating position (FIG. 13). This movement is caused by turning tube 42b shown in FIGS. 1-3 as previously described in connection with those figures.

The blade and blade carriers are also preferably modified to provide a forward cross member having a skid surface for improving blade guidance, for positively resisting downward tilt of the forward end of the carrier, and for facilitating the elimination of any notch in the blade adjacent to the supprting pins. For example, see the modifications shown in FIGS. 16-18, when the blade 20b is like the blades 20 and 20' in FIGS. 4-11 except for elimination of notches 72, 74, 72' and 74', and a possible narrowing of the blade as result of such elimination. The sharpened leading edge 60b of blade 20b is mounted in a vertical plane extending substantially tangent to the trailing sides of pins 16b and 18b which extend inwardly from sidewalls 24b and 26b of the carrier 22b for blade 20b. Said pins and sidewalls correspond to pins 16 and 18 and sidewalls 24 and 26 of carrier 22, except that the cross member 54 between the trailing ends of sidewalls 24 and 26 is replaced by cross member 54b extending integrally between the leading ends of sidewalls 24b and 26b. Cross member 54b has its downwardly facing leading surface 56b curved about axes parallel to the common central axis of pins 16b and 18b, so that it is sloped in the manner of the leading end of the skid surface of a toboggan (see FIG. 1b). The trailing end of surface 56b merges into a horizontal downwardly facing trailing skid surface 58b of cross member 54b, and the side margins of surfaces 56b and 58b merge into the corresponding curved and flat bottom skid surfaces of side members 24b and 26b. As a result, the said skid surfaces 54b and 58b and adjacent skid surfaces of sidewalls 24b and 26b press down on the surface of flesh about to be cut, while sliding onto and over it. The structure of sidewalls 24b and 26b and cross member 54b is preferably formed by bending and forming a single plate of metal or other suitable material. However it could be formed by other means, such as casting.

The forward skid surfaces 56b and 58b ride on the flesh being cut to improve the guidance of blade 20b in response to changes of contour of the flesh being cut. These forward skid surfaces also have the advantage of positively opposing any tendency of the leading end of carrier 22b to tilt down (clockwise about pin 16b as seen in FIG. 16) in response to turning movement about pins 16b further to the rear and thus eliminate the need for any notching of blade 20b adjacent to the pins and reduce production costs. Weld 70b secures blade 20b to sidewalls 24b and 26b without any need for backup against any rear cross member.

While the present preferred embodiments and methods of practicing the invention have been illustrated and described, it will be understood that the invention may be otherwise variously embodied and practiced within the scope of the following claims.

I claim:

1. Apparatus for cutting a strip from a face of a body of flesh, comprising a sheet metal cutting element having a pair of opposite marginal portions projecting from the plane of a flat intermediate portion, a cutting edge extending continuously along said marginal and intermediate portions, a handle having a major elongated portion, means carrying the cutting element, means pivotally connecting the carrying means to one end of the handle, said carrying means having a pair of elongated parallel straight skid surfaces spaced apart and adapted to a slide against a surface of a body in the direction of their elongation while the cutting edge cuts into the body, and said carrying means being secured to said opposite marginal portions of the cutting element so that said cutting edge on the intermediate portion extends generally transversely between said parallel skid surfaces and said intermediate portion extends parallel to the skid surface level, said intermediate portion and parts of said marginal portions and edge of the cutting element being contoured to project beyond the level of said parallel skid surfaces and to form a clear open-ended passage between said level and the projecting parts of the cutting element, said passage being of substantially undiminished cross section from the cutting edge to the trailing end of the intermediate portion which follows during cutting movement, whereby the handle may be operated to press the parallel skid surfaces against a surface of a body of flesh while moving the carrying means along the surface in the direction of elongation of the skid surfaces, thereby causing the edge to cut a strip from the body and causing the successive portions of the strip as they are severed to pass substantialy straight out through the open ended passage between the carrying means and the projecting portion of the cutting element.

2. Apparatus according to claim 1, in which said pivotal connecting means has a pivotal axis extending parallel to a line which extends through and at right angles to the direction of elongation of said skid surfaces.

3. Apparatus according to claim 2, in which said pivotal connecting means permits relative pivotal movement of the handle and carrying means only about said axis.

4. Apparatus according to claim 1, in which said one end of the handle is in the form of a pair of arms movable relative to each other at their ends, said arms and pivotal connecting means being adapted to hold the carrying means on the handle when the arms are moved toward each other, and to release the carrying means from the handle when the arms are moved apart.

5. Apparatus according to claim 4, wherein said arms extend at an angle to the direction of elongation of the handle.

6. Apparatus according to claim 3, in which the handle comprises an inner element connected to the arms and an outer element adapted to be gripped by a hand and surrounding the inner element, said outer element being movable along the inner element in one direction to cause the inner element to move said arms toward each other to connect the carrying means to the handle, and in the opposite direction to disconnect the carrying means from the handle means to hold the outer element in a position where the arms connect the carrying means to the handle, and means to prevent relative rotation between the inner and outer elements while the outer element is in said position.

7. Apparatus according to claim 1, wherein said carrying means comprises a pair of parallel sidewalls with edges forming said parallel skid surfaces, and a cross member between the leading ends of said sidewalls as the carrier advances during cutting, said cross member having a skid surface adapted to press against and slide over the body being cut while said cutting edge follows to cut a strip therefrom.

8. Apparatus according to claim 7, wherein part of said cross member skid surface lies in the plane of said parallel skid surfaces, and another portion of said cross member skid surface is inclined relative to said plane.

9. Apparatus according to claim 1, in which said pivotal connection means includes a pin secured to and projecting from each of said arms to the pin on the other arm, said opposite marginal portions of the blade being notched along one side to fit against said pins and abutted along said opposite sides to press against said cross member whereby the blade is mechanically mounted in the carrying means and is movable therefrom by moving apart the said arms of the handle together with their attached pins.

10. Apparatus according the claim 1, in which said cutting edge is continuously contoured and comprises a pair of parallel short lengths projecting from adjacent said skid surfaces, and a relatively long and substantially straight length extending between and forming corners with the projecting ends of said short lengths, said relatively long length being substantially parallel to a plane through said skid surfaces.

11. Apparatus according to claim 2, in which the cutting edge has a relatively long straight portion extending parallel to said pivotal axis.

12. Apparatus according to claim 1, in which said pivotal connecting means is mounted to position its axis of pivotal movement adjacent the center between the opposite ends of each of said skid surfaces.

13. Apparatus according to claim 12, in which said cutting edge is mounted at or between a first position substantially in a first plane extending at right angles to the skid surfaces and through said pivotal axis, and a second position between said first position and a second plane parallel to said first plane and offset from said plane about half way to the trailing ends of the skid surfaces.

14. Apparatus according to claim 12, in which said cutting edge is mounted substantially in said first plane.

15. Apparatus according to claim 1, in which the handle comprises a pair of arms projecting from one end of the handle and movable relative to each other at their projecting ends, in which the pivotal connection means comprising pin-receiving openings in the carrying means and a pair of pivot pins extending toward each other from the projecting ends of the arms, and in which the handle comprises concentric elements which have inter-engaging helical threads, the arms both being integral with the inner concentric element, and said elements being relatively rotatable to cause relative axial movement between them, and said outer concentric element being thereby relatively axially movable in one direction to move said arms toward each other to connect the carrying means to the handle and in the opposite direction to disconnect the carrying means from the handle.

* * * * *